United States Patent
McAdams et al.

(10) Patent No.: US 9,976,994 B2
(45) Date of Patent: May 22, 2018

(54) SYSTEMS AND APPARATUS FOR REDUCING SIGNAL NOISE DUE TO PUMP OSCILLATIONS

(71) Applicant: DIONEX CORPORATION, Sunnyvale, CA (US)

(72) Inventors: Michael J. McAdams, Los Gatos, CA (US); Ihab Elzind, San Jose, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 15 days.

(21) Appl. No.: 14/839,680

(22) Filed: Aug. 28, 2015

(65) Prior Publication Data

US 2017/0059534 A1    Mar. 2, 2017

(51) Int. Cl.
| | |
|---|---|
| *G01N 30/96* | (2006.01) |
| *G01N 30/64* | (2006.01) |
| *B01D 15/36* | (2006.01) |
| *C02F 1/42* | (2006.01) |
| *G01N 30/16* | (2006.01) |

(52) U.S. Cl.
CPC ............ *G01N 30/64* (2013.01); *G01N 30/96* (2013.01); *B01D 15/361* (2013.01); *C02F 1/42* (2013.01); *G01N 30/16* (2013.01); *G01N 2030/645* (2013.01)

(58) Field of Classification Search
CPC ........ G01N 30/64; G01N 30/66; G01N 30/96; G01N 2030/645
See application file for complete search history.

(56) References Cited

U.S. PATENT DOCUMENTS

| | | | | |
|---|---|---|---|---|
| 4,604,166 | A * | 8/1986 | Weinberg | G01N 27/28 204/400 |
| 4,889,611 | A * | 12/1989 | Blough, Jr. | G01N 27/403 204/411 |
| 5,011,608 | A | 4/1991 | Damjanovic | |
| 5,132,018 | A | 7/1992 | Jones et al. | |
| 5,377,234 | A * | 12/1994 | Robles | G21C 17/022 376/245 |
| 6,623,630 | B1 * | 9/2003 | Staffler | F04B 11/0058 210/198.2 |
| 6,918,595 | B2 | 7/2005 | Proper | |

(Continued)

OTHER PUBLICATIONS

GP50 Gradient Pump Operator Manual, Dionex Corp., Doc. No. 031377, Rev. 03, 168 pages, 2001.

*Primary Examiner* — Natalie Huls (57) ABSTRACT

A system reduces unwanted noise due to pump movement. The system includes a pump including a non-conductive piston extending into a pumping chamber for pumping the sample fluid along an analysis fluid path, a wash chamber, and a seal fluidly separating the pumping chamber from the wash chamber. The system also includes a wash path supplying a wash fluid from a wash reservoir to the wash chamber, an electrical conductor electrically connecting the analysis fluid path to the wash fluid path, and a ground conductor electrically connecting the electrical conductor to ground via a resistor. The electrical conductors and resistor combination between the chambers reduces unwanted noise in the conductivity detector due voltage potentials between the eluent and wash chambers created as the piston moves between the chambers.

29 Claims, 6 Drawing Sheets

(56) References Cited

U.S. PATENT DOCUMENTS

| | | | |
|---|---|---|---|
| 2006/0259015 A1* | 11/2006 | Steinbach | A61M 5/14276 604/891.1 |
| 2008/0135484 A1* | 6/2008 | Hammer | G01N 30/92 210/656 |
| 2009/0218238 A1 | 9/2009 | Dasgupta et al. | |
| 2011/0290726 A1* | 12/2011 | Liu | B01D 19/0031 210/640 |

\* cited by examiner

SYSTEMS AND APPARATUS FOR REDUCING SIGNAL NOISE DUE TO PUMP OSCILLATIONS

TECHNICAL FIELD

This application relates, in general, to systems and apparatus for reducing unwanted noise due to pump movement.

BACKGROUND

High pressure liquid chromatography (HPLC) and ion chromatography (IC) generally require the components of a sample to be separated or analyzed be dissolved in a mobile phase liquid, termed an eluent, and conveyed by that liquid to a stationary phase, that is, a separation column. The separated components may then by analyzed by a conductivity detector downstream from the stationary phase. Piston pumps are often used to supply the liquid and deliver the liquid, with dissolved sample, to the separation column. Such piston pumps are used to withstand extreme pressures and to deliver the liquid at precisely controlled flow rates in a smooth and uniform manner.

In HPLC, such piston pumps may generally include a pump head that have one or more plungers formed of conductive materials such as stainless steel. In IC, such piston pumps generally include pump heads that have one or more plungers formed of non-conductive materials such as sapphire or ceramics. The pump heads also include special high pressure seals that may have lips pressed against the plunger surface by the pressure built up in the pump head, that is, the system pressure. Such pressure seals are described in U.S. Pat. No. 6,623,630 to Staffler, and in U.S. Pat. No. 6,918,595 to Proper.

As the piston moves to aspirate new eluent, small amounts of eluent residing in the head chamber of the pump are commonly transported by the piston surface through the seal to the backside of the seal. Accordingly, such piston pumps often include a wash chamber on the backside of the seal to flush any leakage through the seal. Such wash chambers are generally filled with an aqueous wash solution, which may prevent the growth of salt crystals on the rear side of the seal. The wash solution is sometimes spiked with organic solvent. This organic addition to the wash solution prevents growth of algae and fungi inside the wash chamber.

A voltage potential may be created by the piston moving against the seal and/or by a battery effect from microleakage of the seal. Such voltage potential may undesirably bias the conductivity detector causing unwanted noise on the signal baseline.

In light of the foregoing, it would be beneficial to have systems and apparatuses that overcome the above and other disadvantages of currently available chromatography systems utilizing conductivity detectors and piston pumps.

SUMMARY

One aspect of the present invention is directed to an apparatus for reducing unwanted noise due to pump oscillations including a pump for pumping a sample fluid along an analysis path to a conductivity detector, the pump including a pumping chamber, a piston extending into the pumping chamber for pumping the sample fluid along the analysis path, a seal wash chamber, and a seal fluidly separating the pumping chamber from the seal wash chamber, wherein the piston extends through the seal and creates a voltage potential between the pumping chamber and the seal washing chamber due to transfer of charge and a concentration gradient effect as the piston reciprocates, a wash path supplying a wash fluid from a wash reservoir to the seal washing chamber, an electrical conductor for reducing unwanted noise in the conductivity detector due to pump movement, the electrical conductor electrically connecting the analysis path to the wash path, and a ground conductor electrically connecting the electrical conductor a ground via a resistor.

The piston may be formed of sapphire.

The electrical conductor may be a platinum wire having a first end in electrical communication with the analysis path and a second end in electrical communication with the wash path.

The analysis system may further include a ground conductor electrically connecting the electrical conductor and a ground.

The analysis system may further include a resistor between the electrical conductor and the ground.

The resistor may have a resistance of at least a megaohm resistor.

The ground may be a chassis ground.

The resistor may provide isolation of the analysis path from ground noise while allowing dissipation of floating voltage charge created by the voltage potential between the pumping chamber and the seal washing chamber as the piston reciprocates.

The analysis system may further include a pump body formed of a conductive polyether ether ketone (PEEK) material, wherein the conductive pump body forms the electrical conductor electrically connecting the analysis path to the wash path.

The electrical conductor reduces unwanted cycling in the conductivity detector by reducing any voltage potential across the pumping chamber and the seal wash chamber caused by the transfer of charge and/or concentration gradient effect as the piston reciprocates.

Another aspect of the present invention is directed to an analysis system including an analysis path, a pump for pumping a sample fluid along the analysis path, the pump including a pumping chamber, a non-conductive piston extending into the pumping chamber for pumping the sample fluid along the analysis path, a seal wash chamber, and a seal fluidly separating the pumping chamber from the seal wash chamber, wherein the piston extends through the seal and creates a voltage potential between the pumping chamber and the seal washing chamber due to the transfer of charge as the piston reciprocates, a conductivity detector fluidly connected to the analysis path downstream of the pump for monitoring the sample fluid, a wash path supplying a wash fluid from a wash reservoir to the seal washing chamber, and an electrical conductor for reducing unwanted noise in the conductivity detector due to pump movement, the electrical conductor electrically connecting the analysis path to the wash path.

The analysis system may be an ion chromatography system.

The piston may be formed of sapphire.

The electrical conductor may be a platinum wire having a first end in electrical communication with the analysis path and a second end in electrical communication with the wash path.

The analysis system may further include a polymeric tee assembly having first and second legs extending along the analysis path between the pump and the conductivity detector, and a third leg positioning the first end of the platinum wire in electrical communication with the analysis path.

The analysis system may further include a stainless steel tube forming a portion of the wash path, wherein the second end of the platinum wire is attached to stainless steel tube.

The analysis system may further include a ground conductor electrically connecting a resistor between the electrical conductor and a ground.

The resistor may have a resistance of at least a mega ohm.

The ground may be a chassis ground.

The resistor may provide isolation of the analysis path from ground noise while allowing dissipation of floating voltage charge created by the voltage potential between the pumping chamber and the seal washing chamber as the piston reciprocates.

The analysis system may further include a pump body formed of a conductive polyether ether ketone (PEEK) material, wherein the conductive pump body forms the electrical conductor electrically connecting the analysis path to the wash path.

The pump body may be formed of ultra-high-molecular-weight polyethylene (UHMWPE) containing carbon.

The electrical conductor reduces unwanted cycling in the conductivity detector by reducing any voltage potential across the pumping chamber and the seal wash chamber caused by the transfer of charge and/or concentration gradient effect as the piston reciprocates.

Yet another aspect of the present invention is directed to an ion chromatography system including an analysis path, an eluent source supplying an eluent to the analysis path for forming a mobile phase for chromatographic analysis, an injector for introducing a sample containing an analyte into the eluent to form the mobile phase, a separation column downstream of the injector for separating the analyte, a pump for pumping the eluent to the separation column, the pump including a non-conductive pump body, a pumping chamber in the pump body, a non-conductive piston extending into the pumping chamber for pumping eluent along the analysis path, a seal wash chamber within the pump body, and a seal fluidly separating the pumping chamber from the seal wash chamber, wherein the piston extends through the seal and creates a voltage potential between the pumping chamber and the seal washing chamber by the transfer of charge and/or concentration gradient effect as the piston reciprocates, a conductivity detector fluidly connected to the analysis path downstream of the pump and the separation column to detect analyte flowing along the analysis path through the conductivity detector, a wash path supplying a wash fluid to the seal washing chamber, and an electrical conductor electrically connecting the analysis path to the wash path, wherein the electrical conductor reduces unwanted noise in the conductivity detector due to pump oscillations.

The pump body may be formed of a polymeric material.

The polymeric material may be polyether ether ketone (PEEK).

The piston may be formed of sapphire.

The electrical conductor may be a platinum wire having a first end in electrical communication with the analysis path and a second end in electrical communication with the wash fluid path.

The ion chromatography system may further include a polymeric tee assembly having first and second legs extending along the analysis path between the pump and the conductivity detector, and a third leg positioning the first end of the platinum wire in electrical communication with the analysis path.

The tee assembly may be formed of polyether ether ketone (PEEK).

The ion chromatography system may further include a stainless steel tube forming a portion of the wash path and contacts the wash fluid electrically, wherein the second end of the platinum wire is attached to stainless steel tube.

The resistor may be a megaohm resistor.

The resistor may be a 13 megaohm resistor.

The ground may be a chassis ground.

The resistor provides isolation of the analysis path from ground noise while allowing dissipation of floating voltage charge created by the voltage potential between the pumping chamber and the seal washing chamber as the piston reciprocates.

The methods and apparatuses of the present invention have other features and advantages which will be apparent from or are set forth in more detail in the accompanying drawings, which are incorporated herein, and the following Detailed Description, which together serve to explain certain principles of the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
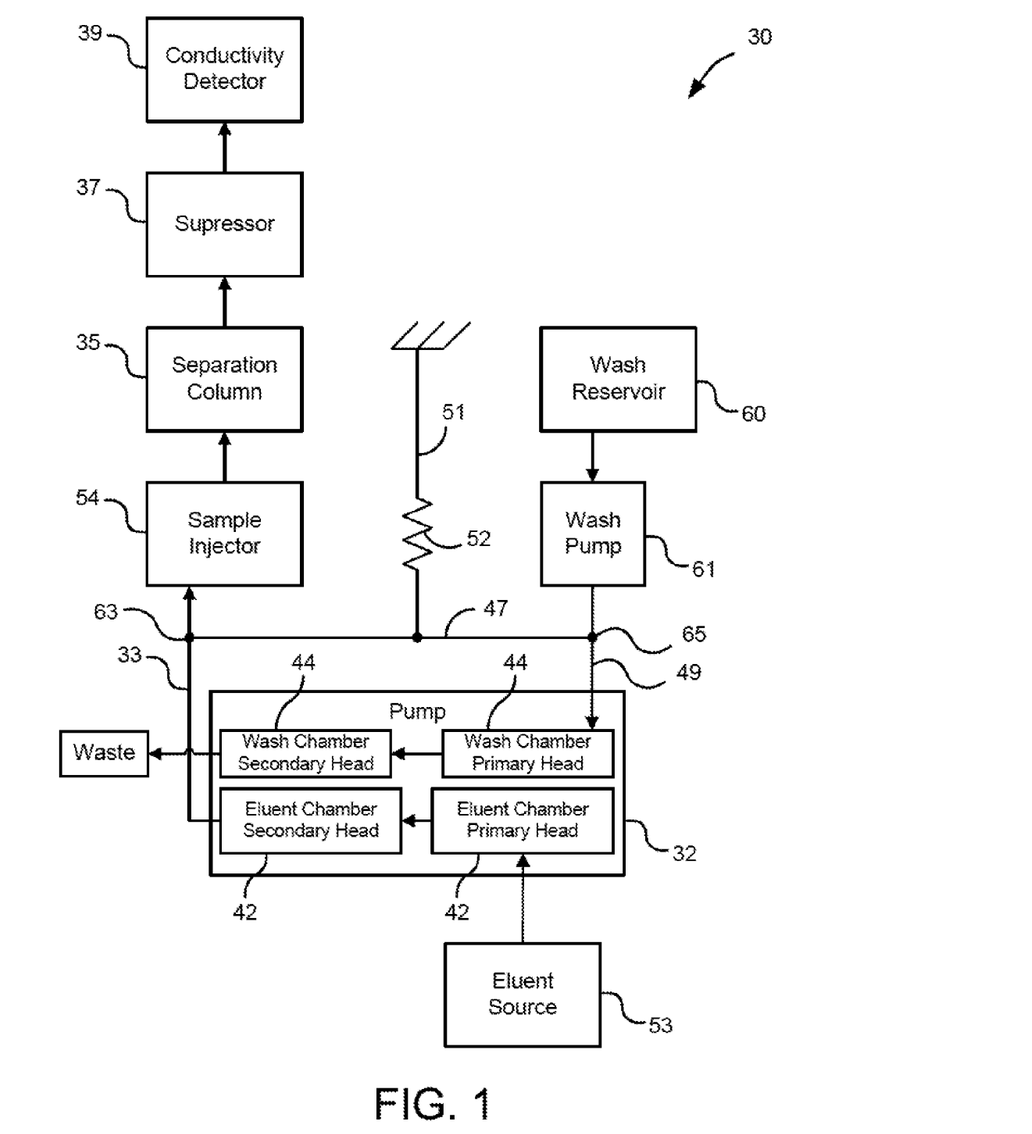
FIG. 1 is a schematic view of an exemplary system for reducing unwanted noise due to pump oscillations in accordance with various aspects of the present invention, the system including a pump having an analysis path extending through eluent chambers and a wash path extending through wash chambers.
Figure 2:
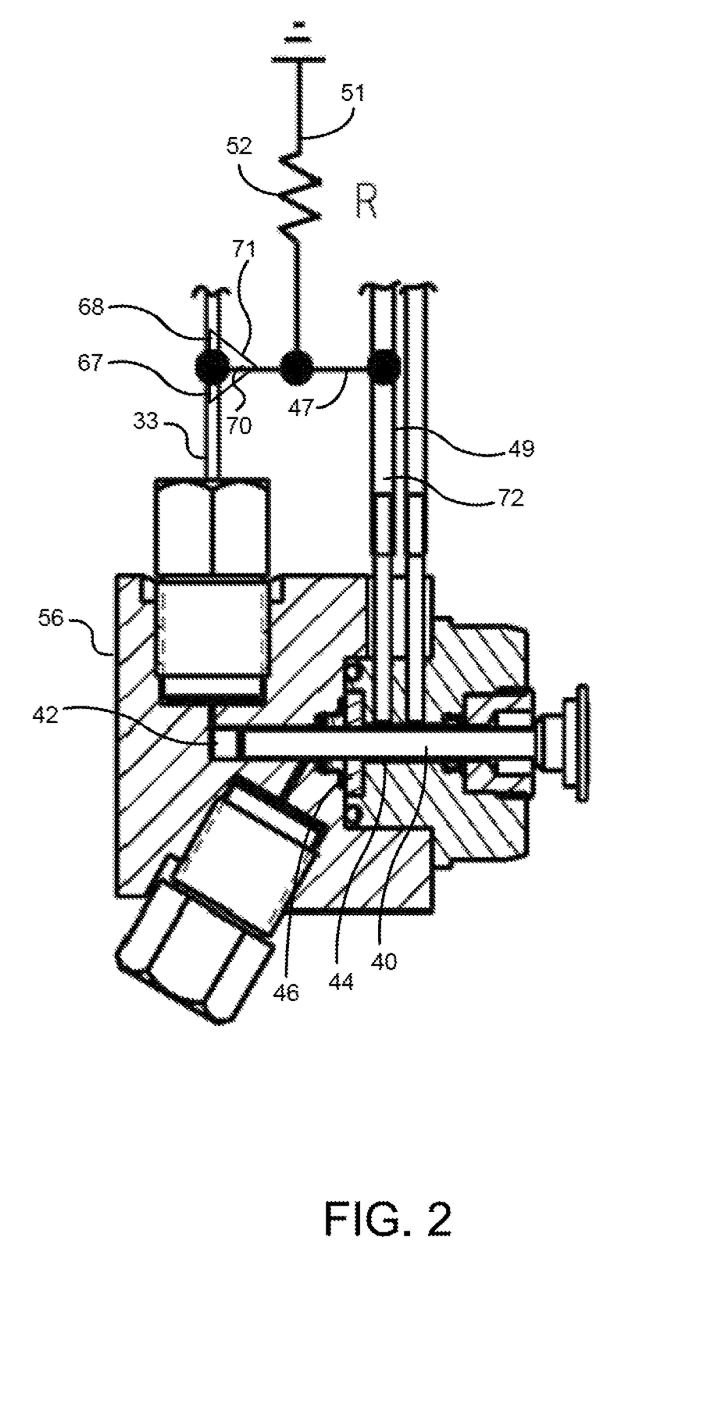
FIG. 2 is a cross-sectional view of an exemplary apparatus that may be utilized in the system of FIG. 1 in accordance with various aspects of the present invention.

Turning now to the drawings, wherein like components are designated by like reference numerals throughout the various figures, FIG. 1 illustrates a system 30 for reducing unwanted noise due to pump oscillations and/or other movement. The system generally includes a pump 32 supplying a sample fluid along an analysis path 33 through a separation column 35 and an optional suppressor 37 to a conductivity detector 39 for analysis of a sample. As shown in FIG. 2, the pump generally includes a reciprocating non-conductive piston 40 pumping eluent through an eluent or pumping chamber 42. The piston also extends through a seal washing or wash chamber 44 that is separated from the eluent chamber by a seal 46. In accordance with various aspects of the present invention, the system is also provided with an electrical conductor 47 connecting the analysis path fluid to a wash path fluid 49 of the wash chamber in order to eliminate a voltage potential created between the eluent and wash chambers as the piston reciprocates. And in accordance with various aspects of the present invention, the system may also be provided with a ground conductor 51 and resistor 52 to isolate the conductivity detector from ground noise while allowing dissipation of floating voltage charge created by the voltage potential between the pumping chamber and the seal washing chamber as the piston reciprocates.

The system is provided with an eluent source 53 for supplying an eluent to the analysis path 33 for forming a mobile phase for chromatographic, and a sample injector 54 for introducing a sample containing an analyte into the eluent to form the mobile phase, which flows to the separation column and optional suppressor for separating the analyte for detection by the conductivity detector.

Figure 5:
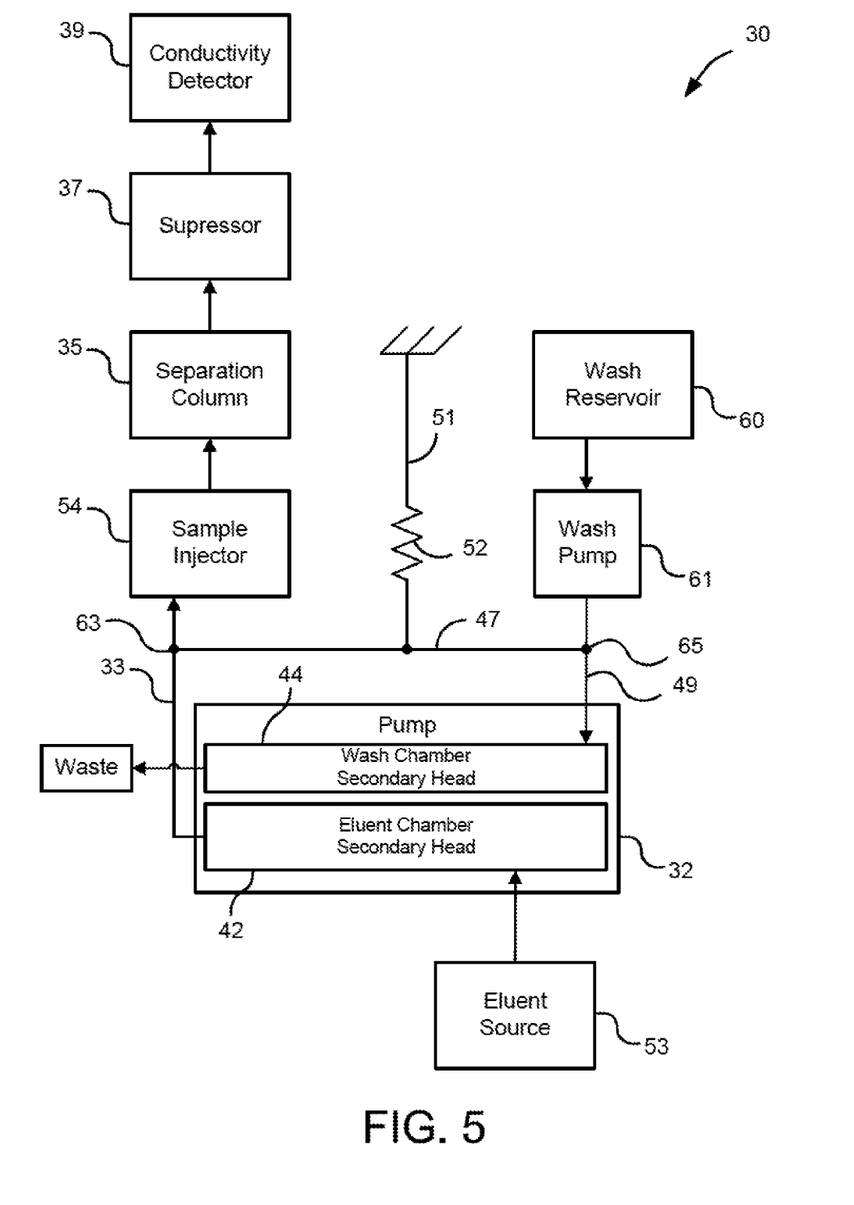
FIG. 5 is a schematic view of an exemplary system for reducing unwanted noise due to pump movement in accordance with various aspects of the present invention similar to that shown in FIG. 1, the system including a pump having an analysis path passing through an eluent chamber and a wash path passing through wash chamber.

In various embodiments, the pump 32 is a piston pump that pumps chromatography eluent and the mobile phase along the analysis path 33 to be delivered to a separation column 35 and conductivity detector 39 in a well-known manner. The pump includes one or more pump heads, each of which includes a reciprocating plunger or piston which operably extends into a high pressure head chamber formed within a housing of the pump that serves as the eluent chamber. For example, FIG. 1 shows a pump with two pump heads, while FIG. 5 shows a pump with a single pump head.

In various embodiments, the pump includes a non-conductive pump body 56 as the various eluents utilized in various chromatography processes are often highly corrosive to metals. Suitable materials for the pump body include, but are not limited to polymeric materials such as polyether ether ketone (PEEK), and/or other suitable materials. Preferably the selected materials have high wear resistance, can endure the corrosive medium and organic solvents used in chromatography, and do not leach ions during chromatographic use. The leaching of ions from metallic materials are known to interfere with ion chromatographic separations.

The piston extends into the eluent chamber for pumping eluent along the analysis path. The piston also extends through the seal wash chamber as well as the seal fluidly separating the eluent chamber from the seal wash chamber. As the piston reciprocates and moves against the seal, it may create a voltage potential between the pumping chamber and the wash chamber by the transfer of charge. For example, when the piston is non-conductive, a voltage potential may be created by the piston moving against the seal and/or by a battery effect from micro-leakage of the seal. This build up may be the result of a concentration cell "battery" made up of the two fluids with different ion concentrations in the respective eluent and wash chambers that are isolated from each other by the seal. Such voltage potential may undesirably bias the conductivity detector causing oscillations on the signal baseline with period corresponding to pump stroke cycles. Also, ions on the surface of the piston may be transferred from one of the seal wash chamber or the eluent chamber to the other chamber that causes a voltage build-up dependent on time. A concentration gradient may develop across the seal as a result of a differing concentration of ions between the eluent chamber from the seal wash chamber and/or the transfer of ions by the piston.

The piston 40 may be formed of sapphire, zirconium, ceramics or other known materials that are suitable for use with the various eluents and samples found in chromatography analysis, which are often highly corrosive to various metal components.

One will also appreciate that leakage between the eluent chamber and the wash chamber may contribute to a voltage potential by the battery effect of a concentration cell described above in the Background. In this regard, the seal separating the two compartments may be somewhat permeable, leaky, or otherwise allow the piston to transfer trace amounts of liquid from one compartment to the other by building up a thin film of fluid on the piston body itself. While such leakage is within conventional manufacturing specifications, such transfer of liquid contributes to such a battery effect and widely known as concentration cell. It should be noted that the seal may act in a manner similar to a salt bridge.

The conductivity detector 39 is fluidly connected to the analysis path downstream of the pump, the separation column and the optional suppressor. The conductivity detector is otherwise conventional in that it detects separated analyte flowing along the analysis path through the conductivity detector.

The wash path 49 supplies a wash fluid to the wash chamber 44 to flush any leakage past the seal 46. The wash path may include a wash reservoir 58 for supplying the wash fluid to the seal washing chamber.

The wash path 49 is a rear seal washing circuit, which generally that extends from a wash reservoir 60, through a wash pump 61 and to the wash chamber 44. In the illustrated embodiment, the wash path is open in that used wash solution goes to waste, however, one will appreciate that the wash path may be closed in which the wash path may return to the wash reservoir.

The voltage potential created by reciprocation of the piston may undesirably cause unwanted noise in the conductivity detector. Undesirable oscillation in baseline readings may be caused by voltage potentials created in PEEK pump heads by the transfer of charge across the UHMWPE seal between the eluent and seal wash fluids. This oscillating voltage potential is conducted through eluent fluid and affects the conductivity measurement system of the conductivity detector.

The amplitude of this voltage potential and thus conductivity signal oscillation varies based on concentration gradient potential across the seal and grounding of the system. Such voltage potential must be neutralized and excess dissipated to eliminate conductivity detector cycling.

Figure 3A:
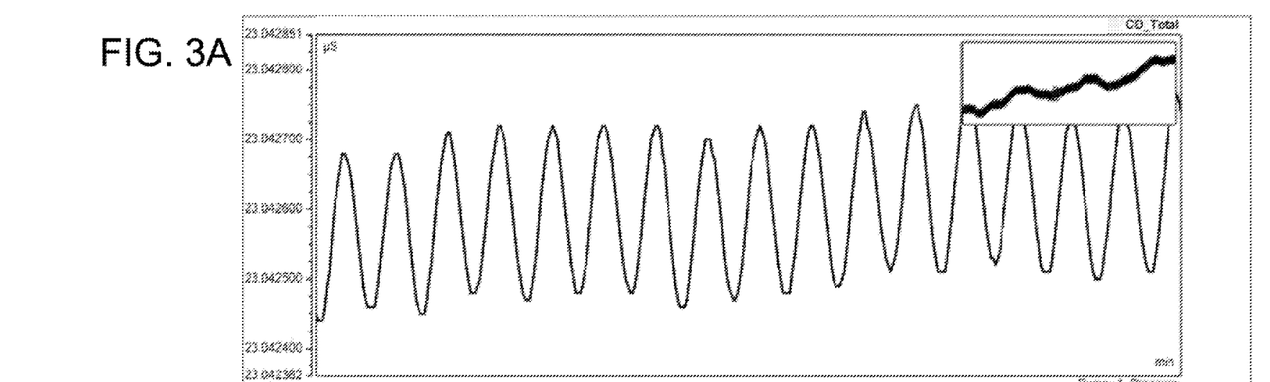
FIG. 3A is a graph showing an amplitude of baseline conductivity signal oscillations due to a voltage potential created between the pumping chamber and the seal washing chamber by the transfer of charge during operation of the pump.
Figure 3B:
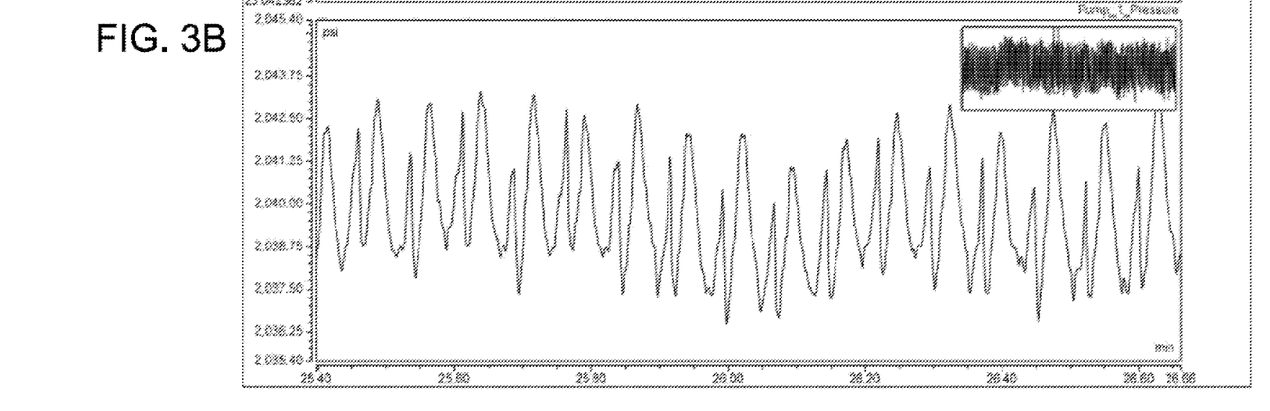
FIG. 3B is a graph showing a pressure trace of the pump corresponding to the amplitude of FIG. 3A.

For example, a voltage potential may form between the eluent and wash chambers that may undesirably bias the conductivity detector causing up to nanosiemen (nS) level oscillations on the signal baseline with a period corresponding to the pump stroke cycles. For example, FIG. 3A is an observed signal oscillation corresponding to the cycling of conductance that was measured in a conductivity detector, while FIG. 3B is a pressure trace (psi) showing the corresponding check valve opening and closing between two pump heads. The double peaks of the graph are due to the overlapping operation of the two pump heads. Thus, as the pump heads reciprocate, an undesired voltage potential may significantly affect measurements of the conductivity detector.

Figure 4A:
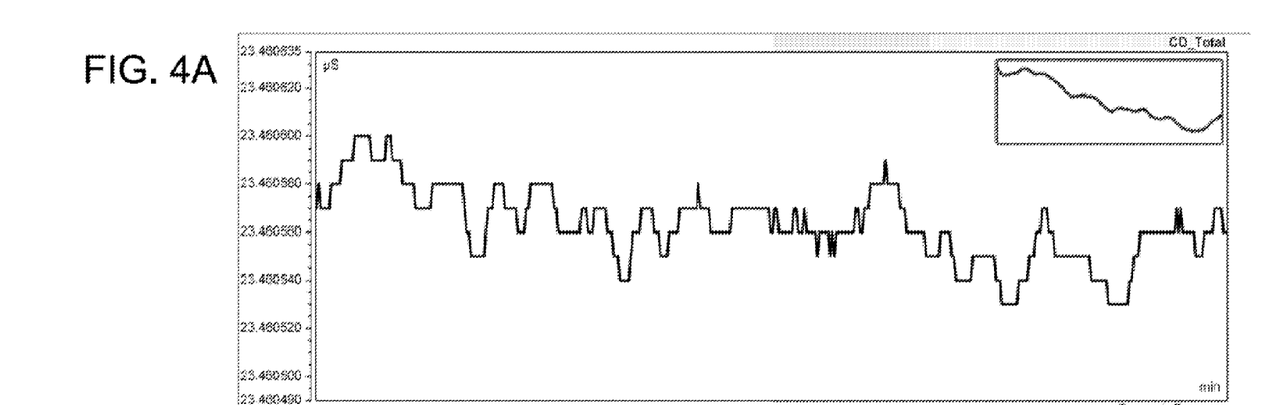
FIG. 4A is a graph showing a baseline conductivity signal during operation of the pump with the analysis path is electrially connected to the wash path.
Figure 4B:
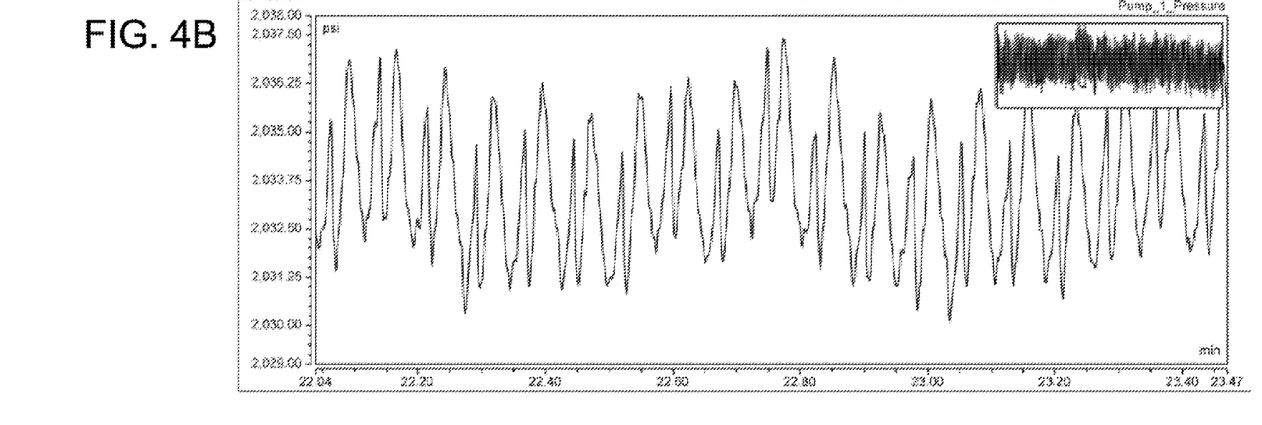
FIG. 4B is a graph showing a pressure trace of the pump corresponding to the amplitude of FIG. 4A.

In accordance with various aspects of the present invention, system 30 is provided with an electrical conductor 47 that electrically connects the analysis path to the wash path to reduce unwanted noise in the conductivity detector due to pump movement. Shorting these two fluid paths reduces the voltage potential between the eluent and wash chambers and thus reduces noise detected by the conductivity detector 39. Shorting the analysis path and the wash path has been found to reduce baseline noise detected by the conductivity detector to random noise in a 10-20 picosiemen (pS) range. For example, FIG. 4A, is an observed signal oscillation corresponding to cycling of conductance that was measured in a conductivity detector when the analysis path 33 and the wash path 49 are shorted to one another, and FIG. 4B is a corresponding pressure trace (psi) similar to that of FIG. 3B showing check valve opening and closing between two pump heads. Again, the double peaks of the graph are due to the overlapping operation of the two pump heads.

The electrical conductor coupling the analysis path to the wash path may be formed of copper, gold, platinum, silver, titanium, or other suitable metals in accordance with the present invention. For example, the electrical conductor may be a platinum wire having a first end 63 in electrical communication with the analysis fluid path 33 and a second end 65 in electrical communication with the wash fluid path 49.

Figure 6:
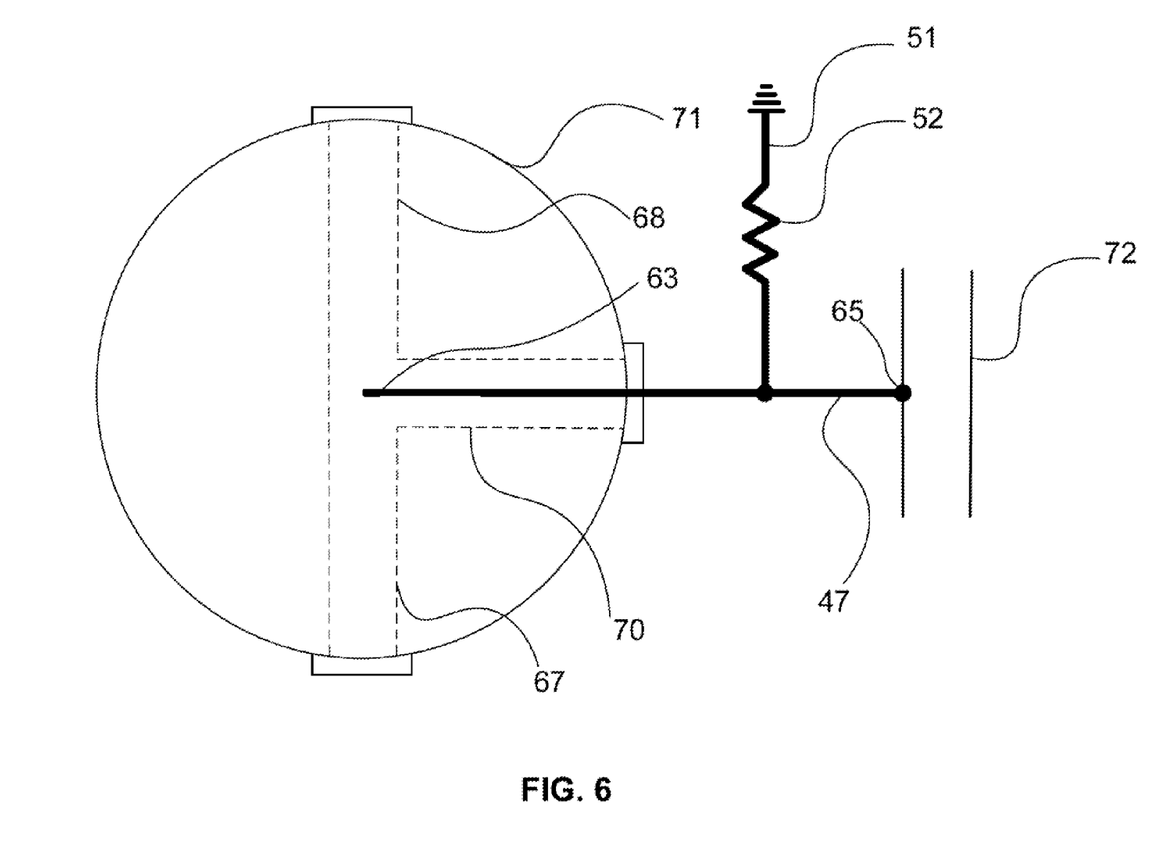
FIG. 6 is an enlarged view of an exemplary polymeric tee connector that may be utilized in the system of FIG. 1 in accordance with various aspects of the present invention.

In various embodiments, a polymeric tee assembly 71 having first and second legs 67, 68 extending along the analysis path between the pump and the conductivity detector, and a third leg 70 positioning a first end 63 of the platinum wire in electrical communication with the analysis fluid path (see FIG. 6). In the illustrated embodiment, first end 63 is in physical contact with the eluent liquid and is in electrical contact with the analysis path, however, one will appreciate that the wire may be in direct or indirect physical contact with the eluent and/or wash fluids provided that there is electrical communication between the wire and the fluids. The tee assembly may be formed of polyether ether ketone (PEEK) and/or other suitable materials compatible with the corrosive qualities of the liquids and solvents commonly used in chromatographic processes.

In various embodiments, a stainless steel tube 72 may form a portion of the wash path in order to provide an electrical path from a second end 65 of the platinum wire to the wash path. Note that second end 65 is in physical and electrical contact with the stainless steel tube 72. However, since stainless steel tube 72 is a conductor, second end 65 is in electrical contact with the wash path and the wash liquid in the wash path.

In accordance with various aspects of the present invention, the ground conductor 51 electrically connects the electrical conductor 47 to ground via a resistor 52. For example a megaohm resistor may be used to isolate the analysis path from ground noise while allowing dissipation of a floating voltage charge that may be created by the voltage potential between the eluent chamber 42 and the wash chamber 44 as the piston 40 reciprocates. Neutralizing and draining the voltage potential from the pump does not require a low resistance connection. While testing has shown that 10-13 megaohm resistors are quite suitable for isolation of the analysis path while dissipating any floating charge that may develop, the resistance is preferably in the range of at least a megaohm, more preferably in the range of 1-100 mega ohms, and more preferably in the range of 1-20 mega ohm, and most preferably in the range of 10-13 mega ohm.

In various embodiments, the ground may be a chassis ground, however, one will appreciate that the ground may be a low impedance ground.

In various embodiments, the pump body 56 or piston 40 may be fabricated from conductive polymeric components and serve as the electrical conductor 47. For example, a pump body formed of conductive PEEK with carbon nanoparticles and/or of conductive UHMWPE with carbon. The eluent and seal wash paths can be electrically connected through these higher resistance materials and may similarly neutralize voltage potential in a manner similar to the platinum wire discussed above.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An apparatus for reducing noise due to pump movement, the apparatus comprising:
   a pump for pumping a sample fluid along an analysis fluid path to a conductivity detector, the pump including a pumping chamber, a piston extending into the pumping chamber for pumping the sample fluid along the analysis fluid path, a seal washing chamber, and a seal fluidly separating the pumping chamber from the seal washing chamber, wherein the piston extends through the seal and creates a voltage potential between the pumping chamber and the seal washing chamber as the piston moves;
   a wash fluid path supplying a wash fluid from a wash reservoir to the seal washing chamber;
   an electrical conductor for reducing noise in the conductivity detector due to pump movement, the electrical conductor electrically connecting the analysis fluid path to the wash fluid path;
   a ground conductor electrically connecting the electrical conductor and a ground; and
   a resistor between the electrical conductor and the ground.

2. The apparatus according to claim 1, wherein the piston is formed of sapphire.

3. The apparatus according to claim 1, wherein the electrical conductor is a platinum wire having a first end in electrical communication with the analysis fluid path and a second end in electrical communication with the wash fluid path.

4. The apparatus according to claim 1, wherein the resistor has a resistance of at least a megaohm.

5. The apparatus according to claim 1, wherein the ground is a chassis ground or a low impedance ground.

6. The apparatus according to claim 1, further comprising a pump body formed of a conductive polyether ether ketone (PEEK) material, wherein the conductive pump body forms the electrical conductor electrically connecting the analysis fluid path to the wash fluid path.

7. The apparatus according to claim 1, wherein the electrical conductor between the paths reduces unwanted cycling in the conductivity detector by reducing any voltage potential across the pumping chamber and the seal washing chamber as the piston moves.

8. An analysis system comprising:
an analysis fluid path;
a pump for pumping a sample fluid along the analysis fluid path, the pump including a pumping chamber, a non-conductive piston extending into the pumping chamber for pumping the sample fluid along the analysis fluid path, a seal washing chamber, and a seal fluidly separating the pumping chamber from the seal washing chamber, wherein the piston extends through the seal and creates a voltage potential between the pumping chamber and the seal washing chamber as the piston moves;
a conductivity detector fluidly connected to the analysis fluid path downstream of the pump for monitoring the sample fluid;
a wash fluid path supplying a wash fluid from a wash reservoir to the seal washing chamber;
an electrical conductor for reducing noise in the conductivity detector due to pump movement, the electrical conductor electrically connecting the analysis fluid path to the wash fluid path, and
a ground conductor electrically connecting a resistor between the electrical conductor and a ground.

9. The analysis system according to claim 8, wherein the analysis system is an ion chromatography system.

10. The analysis system according to claim 8, wherein the piston is formed of sapphire.

11. The analysis system according to claim 8, wherein the electrical conductor is a platinum wire having a first end in electrical communication with the analysis fluid path and a second end in electrical communication with the wash fluid path.

12. The analysis system according to claim 11, further comprising a polymeric tee assembly having first and second legs extending along the analysis fluid path between the pump and the conductivity detector, and a third leg positioning the first end of the platinum wire in electrical communication with the analysis fluid path.

13. The analysis system according to claim 11, further comprising a stainless steel tube forming a portion of the wash fluid path, wherein the second end of the platinum wire is attached to the stainless steel tube.

14. The analysis system according to claim 8, wherein the resistor has a resistance of at least a megaohm.

15. The analysis system according to claim 8, wherein the ground is a chassis ground or a low impedance ground.

16. The analysis system according to claim 8, further comprising a pump body formed of a conductive polyether ether ketone (PEEK) material, wherein the conductive pump body forms the electrical conductor electrically connecting the analysis fluid path to the wash fluid path.

17. The analysis system according to claim 16, wherein the pump body is formed of ultra-high-molecular-weight polyethylene (UHMWPE) containing carbon.

18. The analysis system according to claim 8, wherein the electrical conductor reduces unwanted cycling in the conductivity detector by reducing any voltage potential across the pumping chamber and the seal washing chamber as the piston moves.

19. An ion chromatography system comprising:
an analysis fluid path;
an eluent source supplying an eluent to the analysis fluid path for forming a mobile phase for chromatographic analysis;
an injector for introducing a sample containing an analyte into the eluent to form the mobile phase;
a separation column downstream of the injector for separating the analyte;
a pump for pumping the eluent to the separation column, the pump including a non-conductive pump body, a pumping chamber in the pump body, a non-conductive piston extending into the pumping chamber for pumping the eluent along the analysis fluid path, a seal washing chamber within the pump body, and a seal separating the pumping chamber from the seal washing chamber, wherein the piston extends through the seal and creates a voltage potential between the pumping chamber and the seal washing chamber as the piston moves;
a conductivity detector fluidly connected to the analysis fluid path downstream of the pump and the separation column to detect the analyte flowing along the analysis fluid path through the conductivity detector;
a wash fluid path supplying a wash fluid to the seal washing chamber;
an electrical conductor electrically connecting the analysis fluid path to the wash fluid path, wherein the electrical conductor reduces noise in the conductivity detector due to pump movement; and
a ground conductor electrically connecting the electrical conductor to ground via a resistor.

20. The ion chromatography system according to claim 19, wherein the pump body is formed of a polymeric material.

21. The ion chromatography system according to claim 20, wherein the polymeric material is polyether ether ketone (PEEK).

22. The ion chromatography system according to claim 19, wherein the piston is formed of sapphire.

23. The ion chromatography system according to claim 19, wherein the electrical conductor is a platinum wire having a first end in electrical communication with the analysis fluid path and a second end in electrical communication with the wash fluid path.

24. The ion chromatography system according to claim 23, further comprising a polymeric tee assembly having first and second legs extending along the analysis fluid path between the pump and the conductivity detector, and a third leg positioning the first end of the platinum wire in electrical communication with the analysis fluid path.

25. The ion chromatography system according to claim 24, wherein the tee assembly is formed of polyether ether ketone (PEEK).

26. The ion chromatography system according to claim 23, further comprising a stainless steel tube forming a portion of the wash fluid path, wherein the second end of the platinum wire is attached to the stainless steel tube.

27. The ion chromatography system according to claim 19, wherein the resistor has a resistance of at least a megaohm.

28. The ion chromatography system according to claim 27, wherein the resistance is in a range of 10-13 megaohms.

29. The ion chromatography system according to claim 19, wherein the ground is a chassis ground or a low impedance ground.

* * * * *

UNITED STATES PATENT AND TRADEMARK OFFICE
CERTIFICATE OF CORRECTION

PATENT NO. : 9,976,994 B2  
APPLICATION NO. : 14/839680  
DATED : May 22, 2018  
INVENTOR(S) : McAdams et al.

Page 1 of 1

It is certified that error appears in the above-identified patent and that said Letters Patent is hereby corrected as shown below:

On the Title Page

Column 2 (item (57), Abstract), Line 13: After "due" insert -- to --

Signed and Sealed this  
Twentieth Day of October, 2020

Andrei Iancu  
*Director of the United States Patent and Trademark Office*